United States Patent [19]

Pometto, III et al.

[11] Patent Number: 5,145,779
[45] Date of Patent: Sep. 8, 1992

[54] PROCESS OF BIODEGRADATION OF HIGH MOLECULAR WEIGHT POLYETHYLENE BY AEROBIC LIGNOLYTIC MICROORGANISMS

[75] Inventors: Anthony L. Pometto, III; Byungtae Lee, both of Ames, Iowa

[73] Assignee: Iowa State University Research Foundation, Inc., Ames, Iowa

[21] Appl. No.: 695,546

[22] Filed: May 3, 1991

[51] Int. Cl.$^5$ .................. C12R 1/03; C12R 1/465; C12P 1/04
[52] U.S. Cl. .................. 435/262; 435/170; 435/825; 435/886
[58] Field of Search ............. 435/170, 262; 523/126, 523/124

[56] References Cited

U.S. PATENT DOCUMENTS

| | | | |
|---|---|---|---|
| 3,454,510 | 7/1969 | Newland et al. | 523/126 |
| 3,867,324 | 2/1975 | Clendinning et al. | 523/126 |
| 4,478,747 | 10/1984 | Crawford et al. | 435/72 |
| 4,704,360 | 11/1987 | Shoham et al. | 435/252.5 |
| 4,931,488 | 6/1990 | Chiquet | 523/126 |
| 4,939,194 | 7/1990 | Scott et al. | 523/126 |
| 4,983,651 | 1/1991 | Griffin | 524/56 |

FOREIGN PATENT DOCUMENTS

| | | | |
|---|---|---|---|
| 0216412 | 4/1987 | European Pat. Off. | 523/126 |
| 88/06609 | 9/1988 | PCT Int'l Appl. | 523/126 |

OTHER PUBLICATIONS

Biotech Abs. 91-04216 Gould et al. Pap ACS 200th (1990) Pt 2 PMSE 188.
Biotech Abs. 91-05411 Lee et al. Appl. Envir Microbiol (1991) 57, 3, 678-85.
Biotech Abs. 89-08652 Hays et al. Abs. Pap A.C.S. (1989) 197 Meeting.
Biotech Abs. 89-08675 Gould et al. Abs. Pap A.C.S. (1989) 197 Meeting.
Biotech Abs. 91-04214 Shogren et al. Abs. Pap A.C.S. (1990) 200 Meeting Pt 2.

*Primary Examiner*—Herbert J. Lilling
*Attorney, Agent, or Firm*—Zarley, McKee, Thomte, Voorhees & Sease

[57] ABSTRACT

Biodegradation of deradeable plastic polyethylene by lignin degrading microorganisms.

10 Claims, 4 Drawing Sheets

- ○ ZERO
- ● CONTROL
- ▽ S. VIRIDOPORUS
- ▼ S. BADIUS
- □ S. SETONII

- ○ ZERO
- ● CONTROL
- ▽ P. CHRYSOSPORIUM

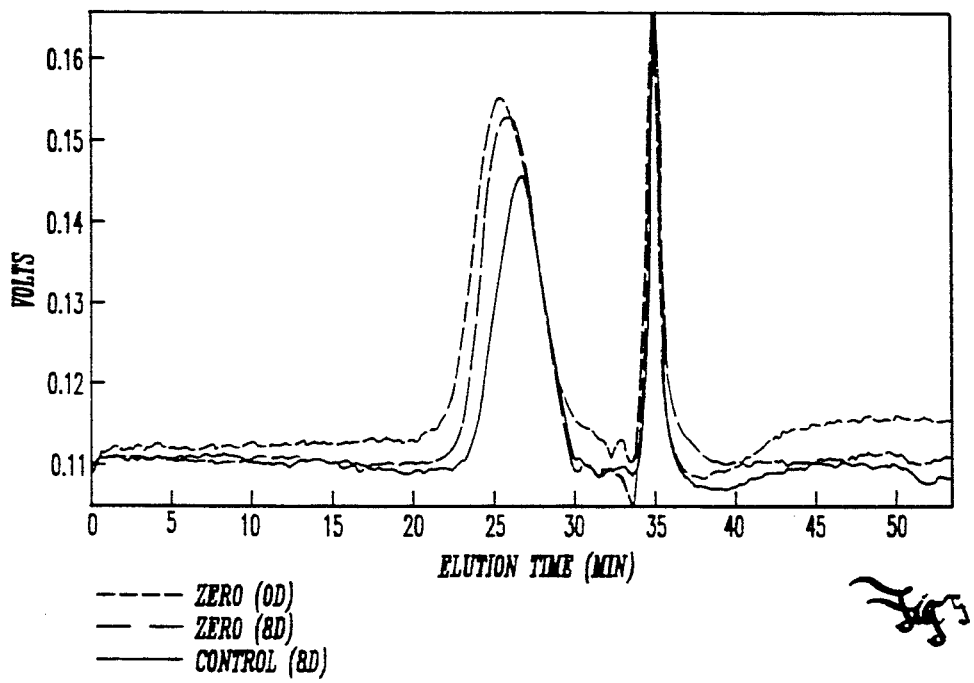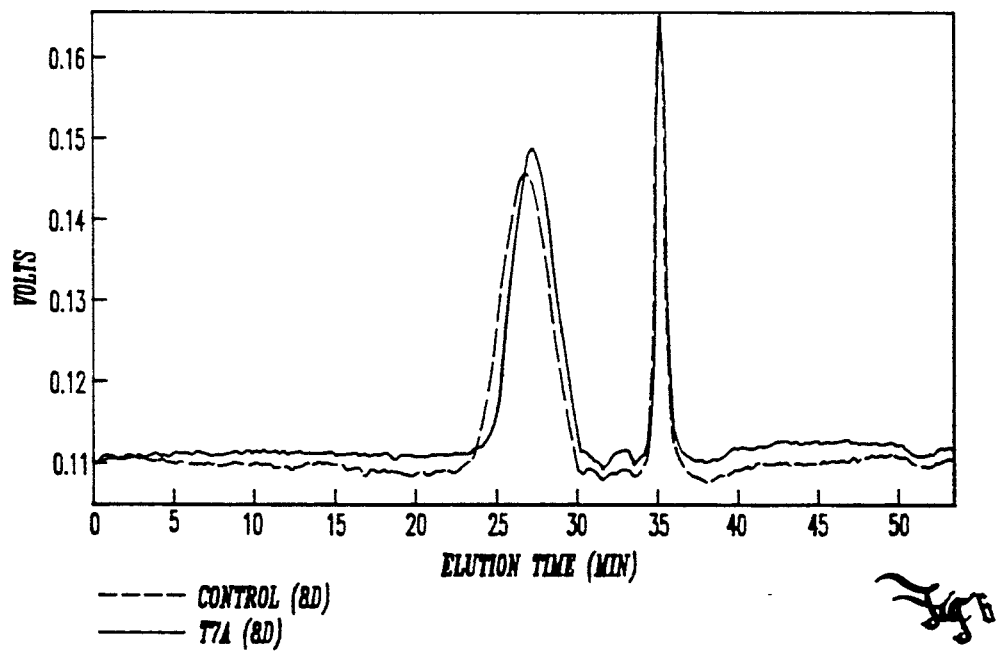

PROCESS OF BIODEGRADATION OF HIGH MOLECULAR WEIGHT POLYETHYLENE BY AEROBIC LIGNOLYTIC MICROORGANISMS

BACKGROUND OF THE INVENTION

Recalcitrant plastics accumulate in the environment at a rate of 25 million tons per year. The fate of these organic polymers in the environment and the time required for their total mineralization to $CO_2$ have yet to be fully understood. There is a growing interest in the development of degradable plastics in landfills and composts. One of the most commonly suggested uses for starch-based degradable plastics is for composting of lawn, garden, and shrub litter, which could reduce the volume of material entering the landfills up to 20%.

The degradable plastic must still retain all of the physical properties expected by the consumer and, then, when placed in the appropriate environment, degrade more rapidly than conventional disposable plastics. To enhance the degradation of the polyethylene, chemical or photo-initiators or both are added to the degradable plastic films. For polyethylene films containing photo- and pro-oxidants, the primary initiators of oxidation are light and temperature, respectively. Both the pro-oxidant and the photo-oxidant produce free radicals on the long polyethylene chain, causing the material to lose some of its physical properties, to become oxidized, and possibly to become more accessible to microbial biodegradation. For further details with regard to conventional polyethylene or other alpha-olefin polymers containing photo- or pro-oxidants to enhance their degradation, see Chanda, M., and S. K. Roy. 1986, Plastic Technology Handbook, Marcel Dekker, Inc., New York; Cornell, J., A. M. Kaplan, and M. R. Rogers, 1984, Biodegradability of Photooxidized Polyalkylenes, J. Appl. Polym. Sci. 29:2581–597. Photo and/or pro-oxidant containing polyethylene is well known and need not be described in detail here. It is common for such polymers to contain amounts of starch polymer to enhance degradation. The amount of starch polymer will range from about 3% to about 12%, with about 6% to about 9% being typical.

While these starch containing polymers, especially those containing either photo- or pro-oxidants as well, are better than the nonstarch polymer containing alpha-olefin polymers from the standpoint of biodegradability, they still are less than totally satisfactory in achievement of the goal of complete biodegradability. Put another way, the polymers tend to remain environmentally persistent. There is, therefore, a continuing need to enhance degradation of alpha-olefin polymers.

There is a particular need to enhance the degradation of high molecular weight polyethylene which is so common in our environment. High molecular weight polyethylene, that is polyethylene having a molecular weight within in the range from about 50,000 to 90,000 or even higher, is particularly environmentally persistent. These materials are commonly produced with linear-low density polyethylene. In sum, the past efforts have not solved the environmental persistence of long chain high molecular weight polyethylene and the potential pollution therefrom.

This invention has as its primary objective, a method and means for enhancing the biodegradability of alpha-olefin polymers, particularly linear low-density polyethylene to $CO_2$. As a result of this invention, the degradable polyethylene can be placed in landfills and composts.

The method of accomplishing the primary objective of the present invention is premised upon the discovery that in the presence of lignocellulose-degrading microorganisms starch containing degradable plastics, in pure culture, resulted in biodegradation of those plastics. Particulars of the method and of achieving the objectives of the invention are disclosed hereinafter.

SUMMARY OF THE INVENTION

High molecular weight polyethylene starch containing plastics are degraded by lignocellulose-degrading microorganisms. The reaction preferably takes place under aerobic conditions. As a result, the lignocellulose-degrading microorganisms can be inoculated into a compost pile containing the starch containing degradable plastic.

BRIEF DESCRIPTION OF THE DRAWINGS

FIGS. 5 and 6. Comparison of HT-GPC chromatograms for 0- and 8- day heat (70° C.) treated degradable plastics after 4 weeks of incubation with ligninolytic microorganisms.

In FIG. 5 Zero (Od) is initial material (zero-time-control), Zero (8d) is 8 days heat-treated material, and Control (8d) is uninoculated 8 day heat-treated material incubated for 4 weeks at 37° C. (uninoculated-control). In FIG. 6 control (8d) is a 8 day heat-treated uninoculated-control, and T7A (8d) is the 8 day heat-treated film incubated with *S. viridosporus* at 37° C. for 4 weeks.

DETAILED DESCRIPTION OF THE INVENTION

Figure 1:
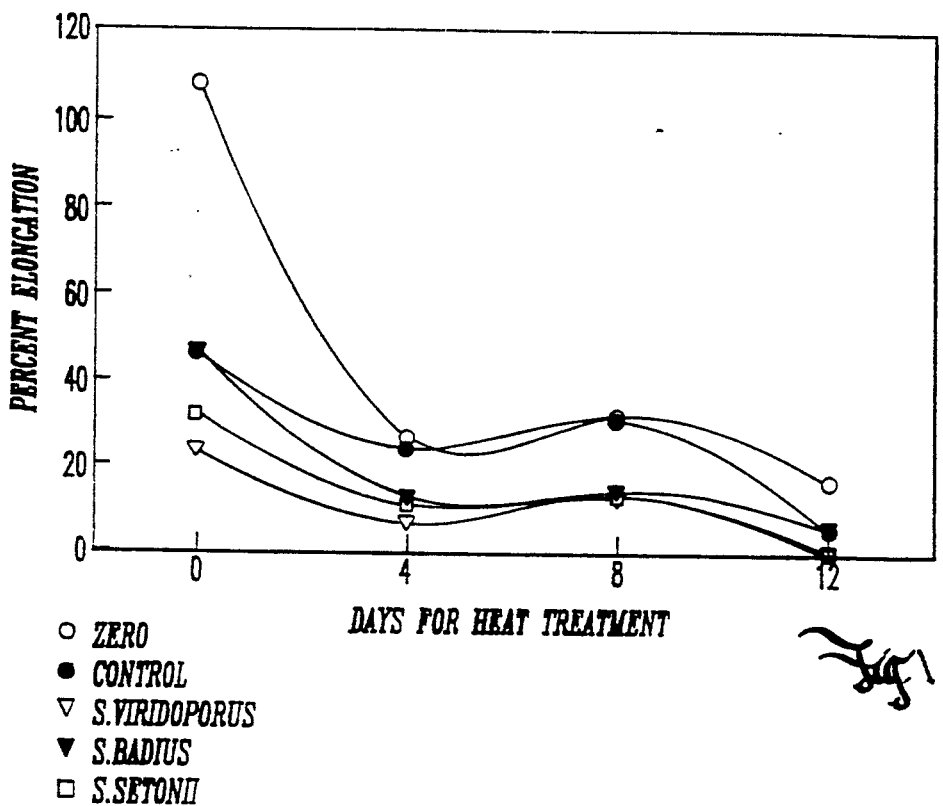
FIG. 1 and 2. Change in percent elongation for 0-, 4-, 8- and 12-day heat-treated (70° C.) degradable plastic films after 4 weeks of incubation in culture media, with and without (control) ligninolytic microorganism. Zero-control is heat treated but not incubated. Each data point represents an average of four replicates.

The present invention is directed to a process of degrading $C_2$ to $C_8$ alpha-olefin polymers up to at least 6000 carbon atoms long. A preferred polymer is polyethylene. Linear low-density polyethylene is, of course, well known and generally refers to polyethylene having a molecular weight within the range of 160,000 to about 260,000 and perhaps even higher. It is particularly difficult to degrade in comparison with low molecular weight materials such as parafins.

As heretofore explained, it is common place to include starch polymer in the polymer complex of linear low-density polyethylene in order to increase biodegradability. The use of corn starch at levels of 3% to 12%, more commonly 6% to 9% is known. It is also known that biodegradability is enhanced by adding either photo- or pro-oxidants. Such oxidants typically include transition metals like iron, copper, manganese, nickel, and a polyunsaturated lipid like soy or corn oil. The presence of oxygen and the pro-oxidant, will initiate free radical formation which eventually results in the oxidation of the polyethylene polymer. This chemical oxidation of the polyethylene initiates biological degradation of the polymer and promotes the starch degradation.

Lignin is a polymer of phenylpropane units that are randomly covalently linked by $\beta$-aryl-ether-bonds. It is an amorphous polymer found in all plant material associated with cellulose, the most abundant organic compound in the biosphere. Lignin is naturally occurring, it is highly complex, and it is a nonrepeating hetropolymer that produces structural support in woody plants. Lignin is generally resistant to attack by most microorganisms. There are, however, some microorganisms that can metabolize lignin. These include some species of fungi and a relatively small number of bacteria.

Known lignin degrading microorganisms, the bacterial variety, include the following: *Streptomyces viridosporus* T7A, *Streptomyces badius* 252, *Streptomyces setonii* 75Vi2, *Streptomyces chromofuscus* A2, Streptomyces diastaticus A3, *Streptomyces rochei* A4, *Streptomyces chromofuscus* A6, *Streptomyces cyaneus* A7, *Streptomyces chromofuscus* A8, *Streptomyces rochei* A10, *Streptomyces chromofuscus* A20, *Streptomyces flavorirens* 28, *Streptomyces cyaneus* MT 813, *Thermomonospora mesophila*, *Actinomadura* sp MT809. The preferred lignin degrading bacteria for use in this invention are *Stretpomyces viridosporus* T7A, *Stretpomyces badius* 252, and *Stretpomyces setonii* 75Vi2.

Examples of lignin degrading fungi include *Phanerochaete chrysosporium*, *Fusarium moniliforme* 279, *Fusarium nivale* 5080, *Fusarium oxysporum* f. sp pini 2380, *Fusarium roseum* 'Crookwell' 1080, *Fusarium roseum* 'Sambucinum' 1180, *Fusarium tricinctum* 179, *Coriolus versicolor*.

Treatment with the lignin degrading bacteria to enhance biodegradability, is accomplished by simply inoculating a compost pile with the bacteria. This is done by adding the bacteria to the compost pile allowing the degradation to occur slowly over a period of time. Because of the lignocellulose degrading ability of these microorganisms no nutrient supplements are required.

The mixture of lignocellulose, starch, water, and the polyethylene is allowed to degrade under aerobic conditions using the lignin degrading microorganisms. As a result, linear low-density polyethylene which has an expected life in a landfill of 200 years can be degraded in relatively short periods of time.

The following examples are offered to further illustrate but not limit the invention.

EXAMPLE 1

(Pure Culture Studies)

The lignocellulose-degrading microorganisms used were the bacteria *Stretpomyces viridosporus* T7A (ATCC 39115), *Stretpomyces badius* 252 (ATCC 39117), and *Stretpomyces setonii* 75Vi2 (ATCC 39116) and the fungus *Phanerochaete chrysosporium* (ME 446). All cultures were maintained on agar slants at 4° C. (13).

The starch-degrading ability of each microorganism was determined by using culture streaks onto starch agar plate containing 1% (wt/vol) native corn starch, 0.05% (wt/vol) yeast extract, and mineral salts solution (13). Each culture was incubated at 37° C. for 1 to 2 weeks. Starch utilization was confirmed by flooding the plates with iodine (10). The results demonstrated starch clearing by *Stretpomyces badius* and *Stretpomyces viridosporus* only. *Phanerochaete chrysoscorium* and *Stretpomyces setonii* did grow on the culture plate, but no clearing of the starch was detected.

Archer-Daniels-Midland POLYCLEAN masterbatch degradable plastic films made with linear low-density polyethylene containing pro-oxidant and 6% starch were used. Pro-oxidants are mixtures of transition metals (i.e., Fe, Zn, Ni, and/or Mn) and lipids (i.e., corn or soybean oil) which are compounded into the final polyethylene product as very low levels. Films were commercially prepared according to Archer-Daniels-Midland recommended specifications. To accelerate the pro-oxidant activity, sheets of degradable plastic were placed in a 70° C. forced-air oven, with both sides exposed to air for a maximum of 20 days. Sheets were removed every 4 days. The sheets were then cut, following the same orientation (opposite to machine direction), into strips (4 by 1 in. [10.16 by 2.54 cm]; 0.06 to 0.07 mm thick).

The disinfection procedure used with each pretreated film consisted of placing the strips into a covered beaker (no more than 15 to 20 strips), adding a fresh solution of universal disinfectant (10) containing 7 ml of Tween 80, 10 ml of bleach, and 983 ml of sterile water, and stirring for 30 to 60 minutes. Each film was removed with sterile forceps and placed into a covered beaker of sterile water, where it was stirred for 60 minutes at room temperature. The films were then aseptically transferred into a standing 70% (vol/vol) ethanol solution and left for 30 minutes. Each film was then placed into a preweighed sterile petri dish. The dishes with films were placed into a incubator at 45 to 50° C. to dry overnight, allowed to equilibrate to room temperature, and weighed to $\pm 0.1$ mg accuracy; the weight of the film was then determined.

Preweighed disinfected films were aseptically added to sterilized culture medium. The medium contained either 0.6% (wt/vol) yeast extract (Difco Laboratories, Detroit, Mich.) in a nitrogen-free mineral salts solution (5.03 g of $Na_2HPO_4$, 1.98 g of $KH_2PO_4$, 0.20 g of $MgSO_4$, $7H_2O$, 0.2 g of NaCl, 0.05 g of $CaCl_2$, $2H_2O$, plus 1 ml of trace element solution [14] per liter of deionized $H_2O$, pH 7.1 to 7.2, or 3.0% (wt/vol) malt extract (Difco) in deionized water (pH 4.5) for the *Stretpomyces* spp. and *P. chrysosporum*, respectively. Films in culture medium were incubated with shaking for 24 h before inoculation to ensure asepsis. Culture medium was inoculated with spores from a specific ligninolytic microorganism and was incubated with shaking at 125 rpm for 4 weeks at 37 and 30° C. for the bacteria and fungus, respectively (7, 15, 16). Four replicates were prepared for each different pretreated film.

Plastic strips were harvested, washed in 70% ethanol to remove as much cell mass form the residual film as possible, dried at 45° C. as just described for 24 h, and equilibrated, and the weights were determined. Each of the different films with and without heat pretreatment was compared with the corresponding uncultured material (zero controls) as well as with uninoculated incubated films (uninoculated controls) in either 0.6% yeast extract or 3% malt extract medium.

Biodegradation was followed by weight loss, changes in tensile strength (the stress measured at fracture of the specimen), percent elongation (the extension of the material under load [ASTM D882-83]), and changes in polyethylene molecular weight distribution. The data analyses were determined by SAS program by using an analysis of variance to ascertain differences between corresponding zero control and uninoculated control (chemical degradation) and for differences between the corresponding uninoculated control and each of the microbial treatments (biological degradation). Values with $p<0.05$ were considered significantly different.

Changes in tensile strength and percent elongation were determined on an Instron model 1011 at room temperature and 500 mm/min with a 5-cm gap. All samples were equilibrated to 50% relative humidity for at least 40 h preceding analysis (ASTM D882-83, Standard Test Method for Tensile Properties of Thin Plastic Sheeting).

A Waters model 150-C (Waters/Millipore Co., Milford, Mass.) high-temperature gel permeation high-pressure liquid chromatograph (HT-GPC) was used to determine changes in the molecular weight distribution for the residual polyethylene. Three identical Waters u-Styragel HT-linear columns, with functional molecular weight ($M_w$) range of 500 to 8,000,000, were used in series. A mobile phase of 1,2,4-trichlorobenzene (GC/GPC grade; Burdick & Jackson/Bacter, Inc., Markeson, Mich.) was used without antioxidant. A flow rate of 1 ml/min and an injection volume of 200 μl were used. Total run time was 55 min per injection, followed by a 5 minute equilibration delay. A refractive index detector was used. Injector, columns, and detector were all held at 140° C., and the solvent pump was held at 50° C. A molecular weight calibration curve was constructed based on nine different narrow-molecular-weight distribution polystyrene standards, with peak molecular weights ranging from 2,700 to 2,700,000. Samples were prepared in 1,2,4-trichlorobenzene containing 200 ppm (20 μg/ml) of Santanox R (Monsanto, Akron, Ohio) as antioxidant and contained 0.15% (wt/vol) polyethylene. Initially, 45-mg. polyethylene samples were added to amber jars along with 30 ml of 1,2,4-tricholorobenzene with antioxidant. The jars were capped and placed in a 150 to 155° C. convection oven for 4 hours with occasional swirling. The dissolved samples were transferred to Waters filter vials, manually filtered through the integral, Teflon housed, sintered stainless-steel filter (0.5 μm) and immediately placed into the HT-GPC autosampler at 140° C. Duplicate injections were run from each sample. Maxima 820 computer software (Waters/Millipore Co.), was used to determine weight-average molecular weight ($M_w$), number-average molecular weight ($M_n$), and polydispersity ($M_w/M_n$) of the polyethylene samples.

Weight-loss data were inconclusive because of bacterial or fungal cell mass accumulation on the films. Usually, a weight gain was measured, but a slight loss of weight by S. badius 252 and S. setonii 75Vi2 was detected for 12 day heat-treated films (1.04% and 0.73%, respectively) and for S. badius 252 for 16 day heat-treated films (1.02%). Uninoculated-controls generally had a weight gain (average 2.0%), which is consistent with thermal oxidation of the polyethylene (4, 5) and water adsorption by the starch.

Figure 2:
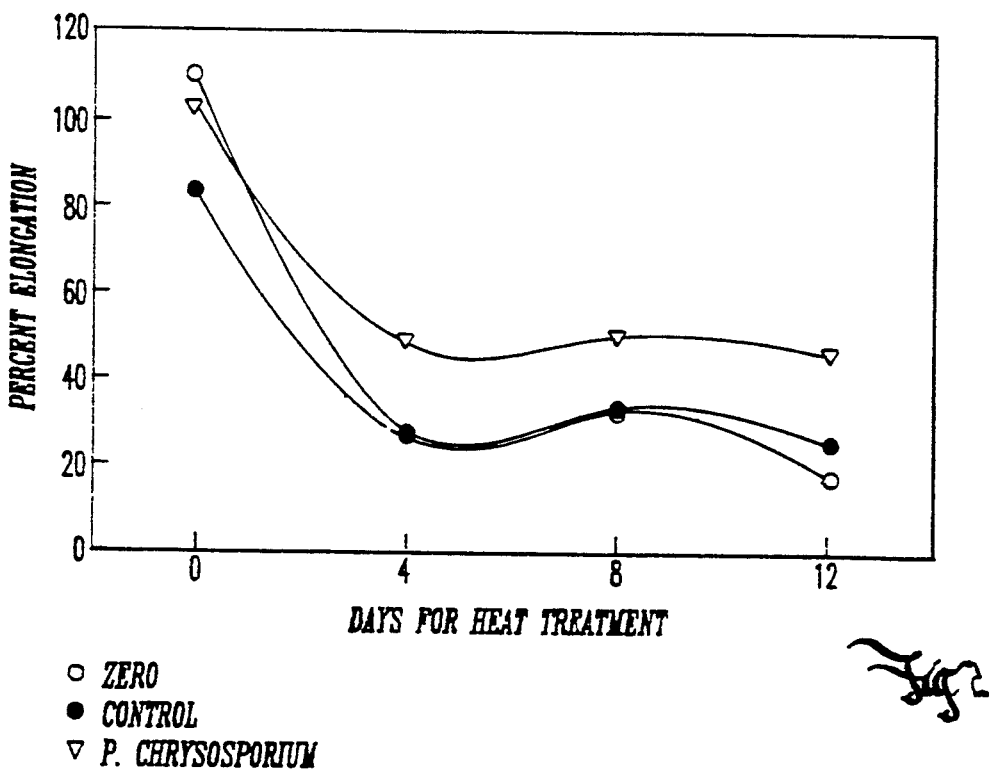

The 16- and 20-day heat-treated samples for the inoculated and uninoculated-controls were too brittle for tensile strength and percent elongation measurements. Tensile strength values for bacteria and fungus indicate little change compared with the zero-control and uninoculated-control samples. The only exception was for the 4 day heat-treated samples with S. viridosporus T7A, which had a 50% reduction in tensile strength compared with the uninoculated-control and zero-control. All the bacterial strains (FIG. 1) demonstrated reductions in the percent elongation values with each of the heat treatments, whereas the fungus caused an increase in percent elongation values (FIG. 2). The initial material (zero-time film with no heat treatment), after a 4 week incubation (uninoculated-controls) in the bacterial and fungal medium, had 47% and 12% reductions in percent elongation, respectively, when compared to the zero-control. Differences in percent elongation between the uninoculated-controls and zero-controls for 4-, 8-, and 12-day 70° C. heat-treated samples were slightly different (range 0%-11%). The bacterial cultures generally showed about a 16% reduction (range 13%-23%) in percent elongation, when compared with their corresponding uninoculated-controls. Only the initial material incubated with S. badius 252 demonstrated relatively no change compared with the controls. However, fungal-cultured heat-treated films consistently demonstrated an increase in percent elongation (range 16%-21%) when compared with their corresponding uninoculated-controls (FIG. 2).

Figure 3:
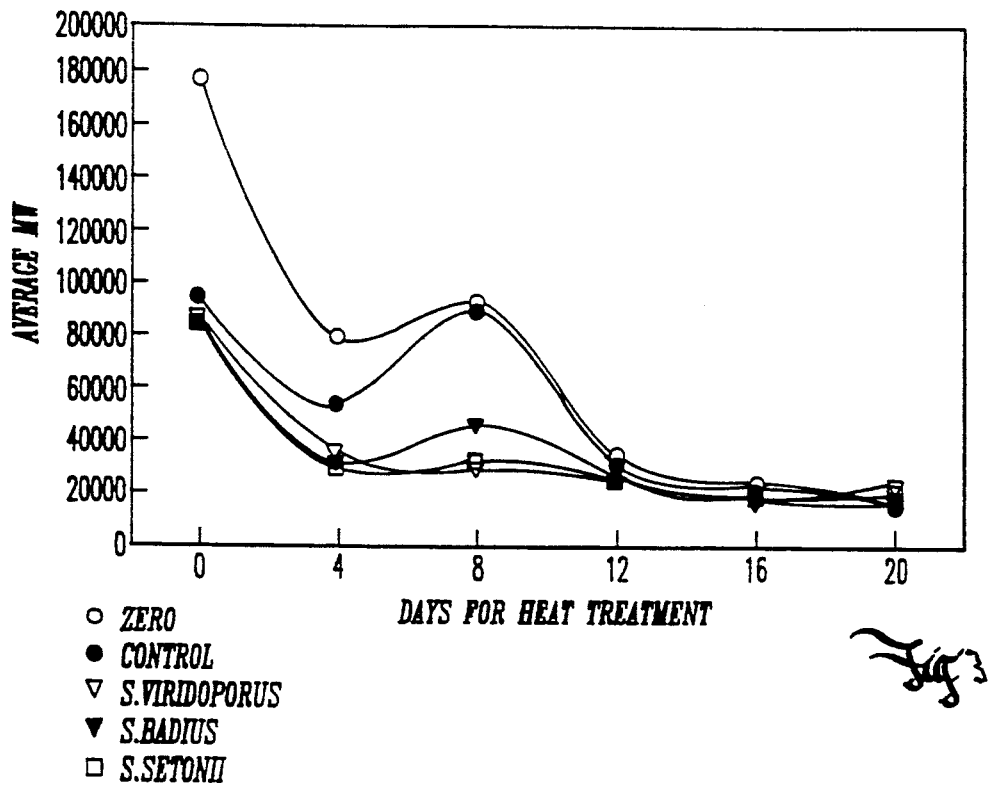
FIG. 3 and 4. The weight-average molecular weight ($M_w$) for 0-, 4-, 8-, 12,-, 16- and 20-day heat (70° C.) treated degradable plastics films after 4 weeks incubation in culture media, with and without (control) ligninolytic microorganism. Zero-control is heat treated but no incubated. Each data point represents an average of four replicates.
Figure 4:
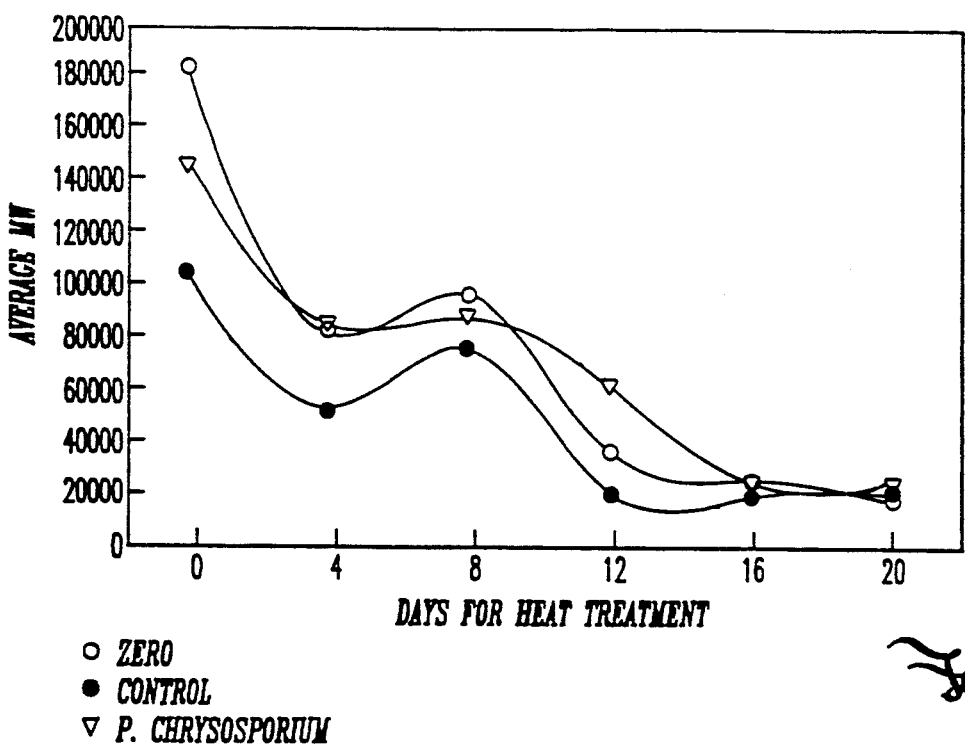

The HT-GPC data were used to evaluate changes in molecular weight distribution of the residual polyethylene films for the different microorganisms and physical treatments (Tables 1 and 2). Changes in weight-average molecular weight ($M_w$) due to heat (70° C.) treatment or corresponding microbial degradation paralleled number-average molecular weight ($M_n$) values. During the 70° C. heat treatment of the initial degradable film (zero-control), the polyethylene $M_w$ dropped dramatically after 4 day heat treatment. This was followed by a slight rise, then a continual reduction. This undulating pattern in $M_w$ is attributed to cross-linking between polymer chains. This same trend, consisting of a slight rise for the day 8 treated film in $M_w$, was observed for the uninoculated-controls and for each of the inoculated films (FIGS. 3 and 4). The $M_w$ for both the fungal and bacterial uninoculated-controls were consistently lower than for the zero-control, with significant ($p<0.05$) differences being determined between the 0-, and 4-day controls. In almost every treatment, the Streptomyces effected a reduction in polyethylene weight-average molecular weight, with significant ($p<0.05$) reduction being determined for the 4- and 8-day heat-treated films (Table 1, FIGS. 3 and 4). S. viridosporus was the overall best, with an average reduction among treatments of 21% (range of 11.8%-67.8%), but there was no significant ($p<0.05$) difference among bacterial treatments. For the 20 day 70° C. heat-treated films S. badius, S. setonii, and Phanerochaete showed a slight increase in $M_w$, whereas S. viridosporus effected no change compared with the control (Tables 1 and 2). Generally, the films incubated with the Streptomyces demonstrated a reduction in polydispersity ($M_w/M_n$), which signifies a narrowing in the overall molecular weight distribution (Table 1). However, this was not the case for the fungal-cultured films (Table 2). Almost all the fungal treatments demonstrated a higher $M_w$ when compared to their corresponding uninoculated-controls with significant ($p<0.05$) differences for 0, 12-, and 20-day heat-treated films. This reduction in polydispersity is illustrated by FIGS. 5 and 6, which display the actual shift in the HT-GPC chromatograms for the initial material zero-time-controls, the 8 day heat-treated zero-control, and the 8 day uninoculated-controls (FIG. 5) and *S. viridosporus*-cultured films (FIG. 6). For each of the controls, the right side of the chromatogram (around 28 minutes) is essentially the same line with a serial reduction in both polydispersity ($M_w/M_n$) and peak height being evident (FIG. 5). However, the bacterial film chromatogram not only is narrower than the controls but is shifted completely to the right (FIG. 6). This shift to the right is indicative of a breakdown of the polyethylene to smaller chain length molecules.

From the results presented, there is strong evidence to support reduction in plastic integrity caused by microbial biodegradation of degradable plastics containing pro-oxidants and 6% starch. It is believed this is the first pure culture study to demonstrate that lignin-degrading microorganisms can actually degrade the high molecular weight polyethylene component of degradable plastics, as indicated by molecular weight reductions.

TABLE 1

Weight-average molecular weights ($M_w$), number-average molecular weights ($M_n$), and polydispersity ($M_2/M_n$) values for specific 70° C. heat-treated degradable plastic with pro-oxidant and 6% starch before and after 4 week shake flask incubation at 37° C. with ligninolytic Streptomyces.[a]

| Days/Type[b] | Zero[c] | Control[d] | S. viridosporus | S. badius | S. setonii |
|---|---|---|---|---|---|
| 0 $M_w$ | 181,379 | 96,828 | 88,701 | 86,303 | 86,098 |
| $M_n$ | 37,395 | 22,050 | 20,738 | 24,738 | 24,462 |
| ($M_w/M_n$) | 4.85 | 4.39 | 4.28 | 3.49 | 3.52 |
| 4 $M_w$ | 81,107 | 54,947 | 36,602[e] | 32,039[e] | 30,586[e] |
| $M_n$ | 17,434 | 17,271 | 11,717 | 10,598 | 10,088 |
| ($M_w/M_n$) | 4.65 | 3.18 | 3.12 | 3.02 | 3.02 |
| 8 $M_w$ | 94,528 | 90,891 | 29,229[e] | 46,661[e] | 32,548[e] |
| $M_n$ | 21,529 | 19,297 | 10,753 | 12,030 | 11,131 |
| ($M_w/M_n$) | 4.39 | 3.99 | 2.72 | 3.80 | 2.92 |
| 12 $M_w$ | 35,127 | 30,909 | 25,486 | 27,731 | 25,641 |
| $M_n$ | 11,036 | 8,550 | 9,158 | 8,849 | 8,354 |
| ($M_w/M_n$) | 3.18 | 3.62 | 2.62 | 3.14 | 3.58 |
| 16 $M_w$ | 23,958 | 19,033 | 17,102 | 21,856 | 18,668 |
| $M_n$ | 8,108 | 6,599 | 7,579 | 8,285 | 8,202 |
| ($M_w/M_n$) | 2.95 | 2.88 | 2.26 | 2.64 | 2.28 |
| 20 $M_w$ | 17,429 | 15,723 | 17,579 | 22,817 | 20,625 |
| $M_n$ | 7,470 | 6,770 | 6,739 | 7,496 | 7,699 |
| ($M_w/M_n$) | 2.33 | 2.47 | 2.61 | 3.04 | 2.68 |

[a] Values were determined by HT-GPC chromatography (see text section). All values represent averages from four replicate plastic strips each obtained from duplicate HT-GPC runs.
[b] Days of heat treatment at 70° C. and average-molecular weight. $M_w$ is the weight-average molecular weight. $M_n$ is the number-average molecular weight. ($M_w/M_n$) is the polydispersity index, which is an indication of the width of the molecular weight distribution for the residual polymer.
[c] Zero values represent specific heat-treated samples without disinfection or cultural incubation (zero-control).
[d] Control values represent specific heat-treated samples that were chemically disinfected and incubated-shaken but were uninoculated (uninoculated-control).
[e] Denotes a significant difference between the $M_w$ for the bacteria as compared to their corresponding uninoculated-control mean $M_w$ with $p < 0.05$.

TABLE 2

Weight-average molecular weights ($M_w$), number-average molecular weight ($M_n$), and polydispersity ($M_w/M_n$) values for specific 70° C. heat-treated degradable plastic with pro-oxidant and 6% starch before and after 4 week shake flask incubation at 37° C. with ligninolytic Phanerochaete.[a]

| Days/type[b] | Zero[c] | Control[d] | P. chrysosporium |
|---|---|---|---|
| 0 $M_w$ | 181,379 | 103,024 | 143,697 |
| $M_n$ | 37,395 | 26,085 | 34,125 |
| ($M_w/M_n$) | 4.85 | 3.95 | 4.21 |
| 4 $M_w$ | 81,107 | 50,341 | 82,988 |
| $M_n$ | 17,434 | 15,327 | 19,690 |
| ($M_w/M_n$) | 4.65 | 3.28 | 4.21 |
| 8 $M_w$ | 94,528 | 73,670 | 85,532 |
| $M_n$ | 21,529 | 17,058 | 20,163 |
| ($M_w/M_n$) | 4.39 | 4.21 | 4.24 |
| 12 $M_w$ | 35,127 | 19,166 | 59,100 |
| $M_n$ | 11,036 | 8,650 | 16,263 |
| ($M_w/M_n$) | 3.18 | 2.22 | 3.63 |
| 16 $M_w$ | 23,958 | 18,107 | 22,994 |
| $M_n$ | 8,108 | 7,866 | 8,926 |
| ($M_w/M_n$) | 2.95 | 2.30 | 2.58 |
| 20 $M_w$ | 17,429 | 19,198 | 23,243 |
| $M_n$ | 7,470 | 8,141 | 8,720 |
| ($M_w/M_n$) | 2.33 | 2.36 | 2.67 |

[a] Values were determined by HT-GPC chromatography. All values represent averages of four replicate plastic strips each obtained from duplicate HT-GPC runs.
[b] Days of heat treatment at 70° C. and molecular weight distribution. $M_w$ is the number-average molecular weight. ($M_2/M_n$) is the polydispersity index, which is an indication of the width of the molecular-weight distribution for the residual polymer.
[c] Zero values represent specific heat treated samples without disinfection or cultural incubation (zero-control).
[d] Control values represent specific heat treated samples that were chemically disinfected and incubated shaken but were uninoculated (uninoculated-control).

EXAMPLE 2

(Culture Filtrate Study)

Streptomyces viridosporus T7A was incubated in 0.6% yeast extract medium (Lee, et al. 1991) at 37° C. with shaking for 48-72 hours. Cell mass was removed by filtration through glass wool. The cell-free filtrate was added to dialysis tubing, submerged in high molecular weight polyethylene glycol (Sigma Chemical Co., St. Louis, Mo.), stored to 4° C. until the volume in the dialysis tubing had reduced from 1,000 ml to <300 ml. A 50 ml volume of concentrated culture-filtrate was added to three 250-ml Erlenmeyer flasks fitted with cotton plugs and covered with aluminum foil, then autoclaved for 15 minutes at 121° C. (control). The remaining 150 ml of culture-filtrate was filter-sterilized using a polycarbonate filter (0.45 μm pore size). Fifty ml samples were aseptically added to three sterile 250-ml Erlenmeyer flasks. To each filter-sterilized culture-filtrate 0.05% sodium azide (Sigma Chemical Co.) was added. Disinfected 8 day 70° C. heat treated 6% starch-/polyethylene films was then added to each flask aseptically (Lee, et al., 1991). Each flask was then incubated with shaking at 37° C. for a total of 3 weeks. Once each week the films were removed from each flask and added to a fresh extracellular concentrate of culture-filtrate (autoclaved or filter-sterilized) from a 48–72 hours culture.

Table 3 shows a summary of the important wavenumbers for FT-IR analysis of degradable plastic changes.

TABLE 3

| Bond type | Wavenumber (cm$^{-1}$) | Structure |
| --- | --- | --- |
| Double bonds | 1640 | —C=C— |
| Ester Carbonyl | 1740 | —COO— |
| Ketone Carbonyl | 1715 | —CO— |
| Alkane | 1465 | —CH$_2$— |
| Terminal Double Bond | 905–915 | —CH=CH$_2$ |
| Carbonyl Index | A1715/A11465 | |
| Double Bond Index | A1640/A1465 | |

All of these groups are found in starch and all could be possible products of oxidative or hydrolytic degradation of polyethylene.

Figure 7:
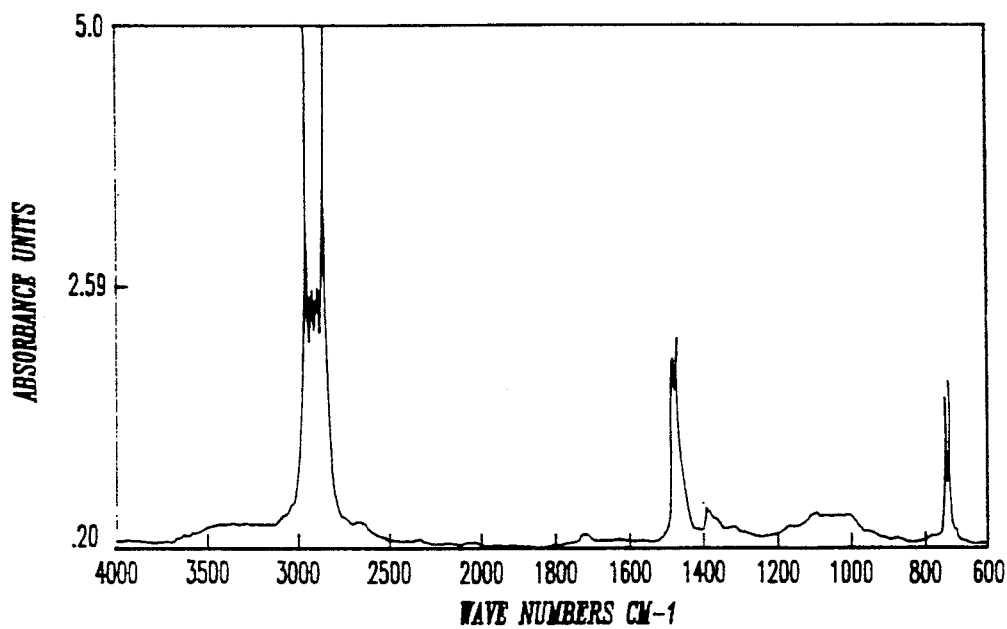
FIG. 7 shows FTIR spectra of 8 day 70° C. heat treated 6% starch/polyethylene films after 3 week incubation with a three fold concentrate of 48 hour *Streptomyces viridosporus* T7A, 0.6% yeast extract culture broth that was autoclaved to kill enzymes (control).
Figure 8:
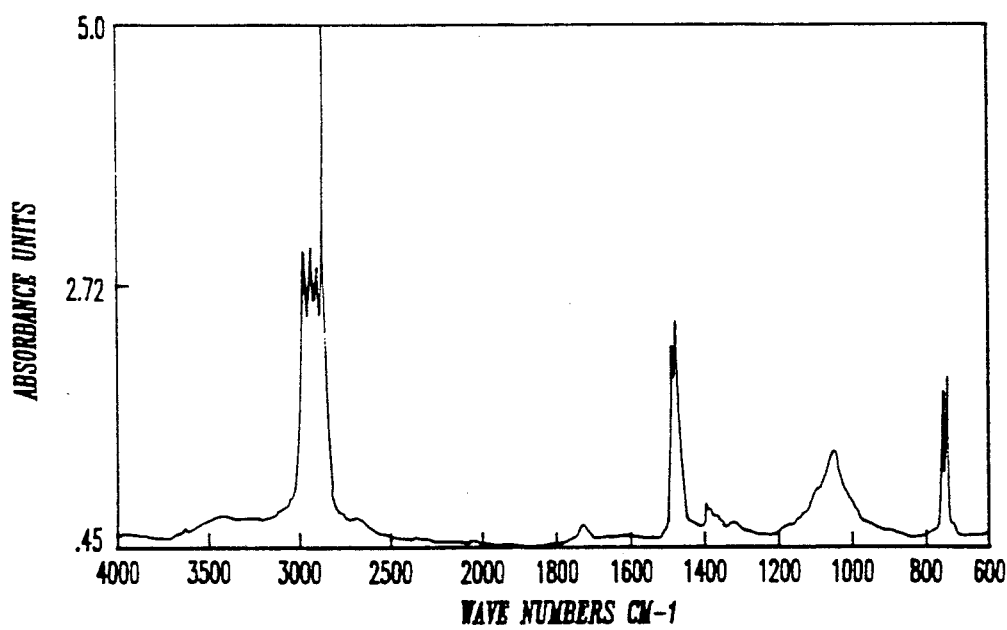
FIG. 8 shows FTIR spectra of 8 day 70° C. heat treated 6% starch/polyethylene films after 3 week incubation with a three fold concentrate of 48 hour *Streptomyces viridosporus* T7A, 0.6% yeast extract culture broth that was filter-sterilized.

The actual mechanism for bacterial biodegradation of polyethylene is unknown. The initiation of the chemical degradation process by the pro-oxidant is required for biodegradation to begin (Lee, et al., 1991). The presence of keton carbonyl groups, however, are not necessarily required for biodegradation according to the FI-IR spectrum (FIG. 7 and 8). Apparently, the more oxidized the polyethylene becomes, the more recalcitrant it is (Lee, et al., 1991). Some extra-cellular enzymatic activity has been demonstrated by using of *Stretpomyces viridosporus* T7A. After a 3 week incubation, films were washed in 70% ethanol, dried and evaluated by FT-IR.

FT-IR spectrometer used was a Bruker Instruments (Billerica, MA) Model IR 113V controlled by Bruker IFS version 12/87 software. Polyethylene films were affixed directly to standard FT-IR sample plates which were made from 1 mm thick aluminum plate. Minimum film size was 2 cm (¾in.) square, although films measuring 1 to 1.25 inch square were more easily attached. Wrinkles in the mounted films were avoided. The spectrum from 600–4000 cm$^{-1}$ was performed for each sample. The regions of interest were summarized in Table 3. The peak appearing around 1700 cm$^{-1}$ indicate polyethylene oxidation.

FIG. 7 and FIG. 8 presents the FI-IR spectrum for two of the films. The enzyme treated film (filter-sterilized culture-filtrate) demonstrate an increase in 1000 cm$^{-1}$, whereas the control film (autoclaved culture-filtrate) demonstrates no change. For the three replicates the FT-IR spectra for all the controls were the same. Only two of the three FT-IR spectra for the T7A enzyme concentrate extract, however, demonstrated the spectral change in the 1000–1100 cm$^{-1}$ region. Starch also absorbs strongly in this region corresponding to the primary and secondary alcohols and aldehydes. filter-sterilized culture-filtrate from 48–72 hour *Stretpomyces viridosporus* T7A culture broth. These extra-cellular enzymes caused a significant change in the FT-IR spectrum for 8 day heat treated degradable plastic (FIG. 7 and 8). This spectral change corresponds to an increase in hydroxyl groups in the plastic, which could be a product of biological degradation. However, the exact mechanism for biodegradation still needs to be characterized.

From the above data and experiments, it can be seen that the invention accomplishes at least all of the stated objectives.

What is claimed:

1. A method for degrading high molecular weight copolymers of alpha-olefins and a starch polymer having a weight average molecular weight at least within the range of 50,000 to 90,000, said method comprising:
   (a) reacting said high molecular weight alpha-olefin starch copolymers with lignin degrading microorganisms selected from the group consisting of *Streptomyces viridosporus* T7A, *Streptomyces badius* 252, *Streptomyces setonii* 75Vi2, *Streptomyces chromofuscus* A2, *Streptomyces diastaticus* A3, Streptomyces rochei A4, *Streptomyces chromofuscus* A6, *Streptomyces cyaneus* A7, *Streptomyces chromofuscus* A8, *Streptomyces rochei* A10, *Streptomyces chromofuscus* A20, *Streptomyces flavoriens* 28, *Streptomyces cyaneus* MT 813, *Thermomonospora mesophila, Actinomadura* sp MT809, and
   (b) allowing the reaction to continue until said polymers are converted to a biologically degraded polymeric material.

2. The method of claim 1 wherein said alpha-olefin is polypropylene.

3. The method of claim 1 wherein said alpha-olefin is linear low-density polyethylene.

4. The method of claim 3 wherein said polymer is a high molecular weight polymer having a weight average molecular weight within the range from about 160,000 to about 260,000.

5. The method of claim 1 wherein said polyethylene contains a starch polymer and a transition metal pro-oxidant.

6. The method of claim 1 wherein the starch polymer is from about 3% to about 12% of the polymer composition.

7. The method of claim 5 wherein said lignin degrading microorganisms is bacteria.

8. The method of claim 1 wherein said lignin degrading bacteria is selected from the group consisting of *Streptomyces viridosporus* T7A, *Streptomyces badius* 552, and *Streptomyces setonii* 75vi2.

9. The method of claim 1 wherein a first step comprises oxidation degrading of said alpha-olefin which is a C$_2$ to C$_8$ alpha olefin prior to reacting said alpha-olefin with said lignin degrading microorganism.

10. The method of claim 6 wherein said organism is a fungi selected from the group consisting of *Phanerochaete chrysosporium, Fusarium moniliforme* 279, *Fusarium nivale* 5080, *Fusarium oxysporum* f. sp pini 2380, *Fusarium roseium* 'Crookwell' 1080, *Fusarium roseum* 'Sambucinum' 1180, *Fusarium tricinctum* 179, *Coriolus versicolor*.

* * * * *